United States Patent [19]

Kelly et al.

[11] Patent Number: 5,483,961
[45] Date of Patent: Jan. 16, 1996

[54] MAGNETIC FIELD DIGITIZER FOR STEREOTACTIC SURGERY

[76] Inventors: Patrick J. Kelly, 620 9th Ave.; Stephan J. Goerss, 5525 St. Mary's Dr. NW., both of Rochester, Minn. 55901

[21] Appl. No.: 297,427

[22] Filed: Aug. 29, 1994

Related U.S. Application Data

[63] Continuation of Ser. No. 34,362, Mar. 19, 1993, abandoned.
[51] Int. Cl.$^6$ ................................ A61B 5/055; A61B 6/03; A61B 17/00
[52] U.S. Cl. ............................... 128/653.1; 128/653.2; 606/130
[58] Field of Search ..................... 128/653.1, 653.2, 128/653.5; 601/4; 606/130; 364/413.13

[56] References Cited

U.S. PATENT DOCUMENTS

| | | | |
|---|---|---|---|
| 4,571,834 | 2/1986 | Fraser et al. | 128/782 |
| 5,042,486 | 8/1991 | Pfeiler et al. | 128/653.1 |
| 5,050,608 | 9/1991 | Watanabe et al. | 128/653.1 |
| 5,078,140 | 1/1992 | Kwoh | 128/653.1 |
| 5,107,839 | 4/1992 | Houdek et al. | 606/130 |
| 5,143,076 | 9/1992 | Hardy et al. | 606/130 |
| 5,186,174 | 2/1993 | Schlöndorff et al. | 606/130 |
| 5,197,476 | 3/1993 | Nowacki et al. | 601/4 |
| 5,211,165 | 5/1993 | Dumoulin et al. | 128/653.1 |
| 5,251,127 | 10/1993 | Raab | 606/130 |
| 5,257,998 | 11/1993 | Ota et al. | 606/130 |
| 5,273,039 | 12/1993 | Fujiwara et al. | 606/130 |
| 5,281,232 | 1/1994 | Hamilton et al. | 606/130 |
| 5,285,787 | 2/1994 | Machida | 606/130 |
| 5,309,913 | 5/1994 | Kormos et al. | 606/130 |

FOREIGN PATENT DOCUMENTS

| | | | |
|---|---|---|---|
| 2007702 | 1/1992 | European Pat. Off. | 606/130 |
| 2006645 | 4/1992 | European Pat. Off. | 606/130 |

*Primary Examiner*—Krista M. Zele
*Attorney, Agent, or Firm*—Curt Harrington

[57] ABSTRACT

The present invention enables stereotactic surgery with a minimal structure present in order to facilitate surgery yet with enhanced accuracy in stereotactic imaging assistance to the surgeon. This device and method is known as "frameless" stereotaxis system, and uses coordinate referencing between the CT or MRI scans and a stereotactic referencing system which uses an electromagnetically driven system (transmitter and receiver) to determine the location of a stylus.

Magnetic field distortion is reduced through the use of a low frequency magnetic field. The frame of reference through which this system operates is coordinate referenced to the coordinates of a composite image formed from a CT, MRI, or other system which are arranged and may be generated in two or three dimensional fashion in response to the position of a pointer as they are referenced to the orientation of a patient during an operation. In the present device and method, registration of the scan images illustrating the lesion, with the physical position of the patient is performed by first synchronizing to two coordinate systems, which can be performed in several ways, including the calibration of the stylus to several landmarks on the patient's anatomy.

5 Claims, 3 Drawing Sheets

MAGNETIC FIELD DIGITIZER FOR STEREOTACTIC SURGERY

This a continuation of application Ser. No. 08/034,362 filed on Mar. 19, 1993, now abandoned.

FIELD OF THE INVENTION

The present invention relates to the field of imaging devices which produce images based on non-invasive methods such as computed tomography, magnetic resonance imaging and ultrasonography. More specifically, the present invention relates to a system for manipulatively displaying images in the operating theater and indicating the position on those displayed images of a magnetic field probe manipulable by a surgeon, especially to assist in locating problem areas during the performance of surgery.

BACKGROUND OF THE INVENTION

The term stereotaxis describes a technique, most often applied to the nervous system, in which the contents of the patient's skull (or body) are considered in a precise three dimensional space defined by a measuring instrument, such as a stereotactic frame, which is fixed to the patient's skull or body. Stereotactic frames are mechanical devices typically based upon a Cartesian or polar coordinate system. These systems typically include a means for securing the stereotactic frame device to the patient, at least one measuring scale for determining and confirming target coordinates and probe trajectories, and a probe holder/carrier.

The probe holder/carrier directs a surgical probe or some other instrument to a desired three dimensional location within the work space which is defined with respect to the geometry of the stereotactic frame. In practice, the stereotactic frame is also used to position a probe or other instrument inside the body into an anatomic or pathologic structure. The frame coordinates of the target structure are determined from stereotactic imaging studies including Computed Tomography (CT), Magnetic Resonance Imaging (MRI), ultrasonography, etc., and radiographically based procedures such as positive contrast ventriculography, or stereotactic atlases.

The use of stereotactic methods in the management of human brain tumors was first proposed in the early 1900's by the British physiologist, Robert Henry Clarke. Clarke patented a device for human stereotactic neurosurgery in 1912. However, the first human stereotactic procedure was not performed until 1947 when Spiegel and Wycis of Philadelphia attempted a ventriculography based dorsal median thalamotomy for psychiatric disease. Stereotactic instruments, methods and indications rapidly evolved thereafter. The three dimensional locations of intracranial targets were determined by means of stereotactic radiographically based methods, most commonly positive contrast ventriculography and stereotactic atlases based on the identification of radiographically established intracranial landmarks. The most common clinical use of stereotactic instrumentation in the late 1950's and 1960's was the placement of subcortical lesions to treat movement disorders, primarily the tremor of Parkinson's disease. However, following the introduction of L-Dopa in 1968 indications for stereotaxis decreased and the number of stereotactic procedures declined precipitously.

Nevertheless, old concepts in stereotactic frame design which were influenced by radiographically based point-in-space procedures carried over into the next phase of evolutionary stereotaxis. The advent of CT scanning in the early 1970's, and later magnetic resonance imaging, MRI scanning, rekindled interest in stereotactic surgery for two reasons: First, Computed Tomography (CT) and Magnetic Resonance Imaging (MRI) provided a precise three dimensional data base which could be incorporated into the three dimensional coordinate system of a stereotactic frame. Secondly, in contrast to radiographically based examinations, one could actually see the complete intracranial tumors on these new computer based imaging modalities.

A progressive and expanding interest in CT and MRI based stereotactic procedures for intracranial tumors and other indications has been noted in neurosurgery since late 1979. Old stereotactic frames were modified to provide CT and MRI compatibility. New imaging compatible stereotactic frames were developed and introduced into the medical market. Nonetheless, the old concept of the stereotactic frame as a rigid device fixed to the patient's skull which was used to mechanically direct probes and other instruments to defined intracranial target points, persisted.

However, in the contemporary era of CT-and MRI-based stereotaxis, the coordinates for the intracranial target are derived from stereotactic CT and MRI examinations instead of a data base consisting only of projection radiographs. But during the stereotactic CT and MRI examinations the patient's head must still be fixed in the rigid, confining, stereotactic frame. CT and MRI opaque external fiducial reference marker systems are frequently applied to the frame to facilitate and simplify the calculation of stereotactic coordinates from the imaging modalities.

The mechanical constraints of a rigid stereotactic frame and the complexity of the computer-based imaging data bases act to limit most contemporary stereotactic procedures to point-in-space targets for biopsy, placing interstitial catheters, localizing a bone flap over a tumor and the like. However, the availability of high capacity and low cost computer work stations have provided a method for reducing the complexity of the image reconstructions and target point cross registration between imaging modalities.

In addition, computer interactive stereotactic methods allow tumors defined by CT and MRI to be considered as volumes in space and provide to surgeons graphical displays which indicate the CT and MRI defined boundaries of the lesion within a defined stereotactic surgical field. This volumetric display technique is superior because it is necessary to remove the entire volume of the tumor, especially at its outer boundary, to ensure that further growth does not take place after the operation.

Such technique for volumetric stereotaxis was first proposed by Kelly et al in 1982. In these procedures, a tumor volume is reconstructed from stereotactic CT or MRI data and reformatted along a surgical viewing trajectory defined by a stereotactic frame. During surgery, an operating room computer system displays cross sections of the reformatted tumor volume with respect to surgical instruments directed into the surgical field using the stereotactic frame as a reference source. Intra-operatively, the surgeon monitors the computer generated image of the surgical field which was derived from CT or MRI scans, as well as the surgical field itself.

In 1986 a system was developed for superimposition of the computer image upon the surgical field by means of a heads-up display unit attached to the operating microscope. This allowed the surgeon to simultaneously view updated reformatted and scaled images of the CT or MRI defined surgical field visually superimposed upon the actual surgical field. Since 1984 over 2300 computer-assisted stereotactic procedures and more than 800 computer-assisted volumetric stereotactic tumors resections have been performed at the Mayo Clinic. It has been found that these procedures allow a more complete removal of a tumor in a minimally invasive way.

However, stereotactic systems to date have had a series of associated problems. Stereotactic frames are cumbersome in general. They are especially cumbersome for procedures requiring more than a few target points and in volumetric stereotactic procedures where the demands of the procedure dictate the need for a larger working area, yet where such demand comes into conflict with the physical structure of the frame. A conventional stereotactic frame is typically a cage structure extending about the patient's head and therefore inherently restricts the freedom of movement of the surgeon. Changing a target point or trajectory to reach that new target point involves a separate mechanical adjustment of the stereotactic frame. This is not usually a problem in point-in-space stereotaxis, as in biopsy procedures for example.

But many mechanical adjustments become very cumbersome when a surgeon is confronted with an infinite number of points which define the boundary of a volumetric lesion. In addition, a stereotactic reference frame must be applied to a patient's head in order to acquire a pre-surgical data base.

Some surgeons find the stereotactic frame application procedure difficult and time consuming. Patients also find this uncomfortable. In addition, the necessity to repeat CT and MRI examinations for the pre-surgical data base increases the cost to the patient. Finally many surgeons are intimidated by mechanically complex devices in general and stereotactic frames in particular. Furthermore, although the mathematics in stereotaxis are understandable, many surgeons are uncomfortable with these also.

Since 1987 there has been an interest in so-called frameless stereotactic procedures. In the procedures described so far, a multi-jointed digitizing arm is indexed to the patient's head. Typically, precision potentiometers or optical encoders on each of the joints of the digitizing arm provide feedback from which real world coordinates of a three dimensional point are determined by a host computer system.

In some systems, reference marks are placed on the patient's scalp. Imaging studies are performed at surgery. The surgeon uses the digitizing arm to touch these registration points. The coordinates of these known points correspond to reference marks on the imaging studies. The computer can then calculate a transformation matrix to allow transformation of the real world coordinate system to the coordinate system of the imaging study. In practice, a cursor, which corresponds to the position of the tip of the pointer in the surgical field, is displayed on CT or MRI slices or three dimensionally rendered images based on CT or MRI.

The problem with these multi-jointed digitizing devices is that they also are cumbersome and restrict the surgeon's freedom of movement. In addition, the 5 or 6 encoders at each of the 5 or 6 joints in the multi-jointed digitizing device can occasionally combine to form a significant non-offsetting error resulting in unpredictable results in surgery.

Although advances in technology include faster hardware and software, improved error detection and improved mathematical treatment in the techniques of producing the images produced and better resolution with respect to individual images selected from an object to be scanned, few such improvements have been directed toward the surgical practitioner to facilitate his working through the procedure. Such improvements are needed to balance the improvements in hardware and software to improve the overall effectiveness of the surgeon's skill.

Several advances in the software and hardware areas have been made, however none enable the effective use and manipulation of two dimensional imaging system as keyed to a three dimensional locational system to be used with a patient during surgery. The following patents outline some of these improvements.

U.S. Pat. No. 4,849,692 issued on Jul. 18, 1989 to Ernest B. Blood and entitled "Device for Quantitatively Measuring the Relative Position and Orientation of Two Bodies in the Presence of Metals Utilizing Direct Current Magnetic Fields" uses two or more transmitting antenna of known position and orientation. Each transmitting antenna is driven, one at a time by a pulsed direct current signal. The receiving antenna measure the transmitted signals, one axis at a time, and then measures the earth's magnetic signal, one axis at a time.

U.S. Pat. No. 4,945,305, issued on Jul. 31, 1990 to Ernest B. Blood and also entitled "Device for Quantitatively Measuring the Relative Position and Orientation of Two Bodies in the Presence of Metals Utilizing Direct Current Magnetic Fields" describes improvements to the '692 patent and improved locational and orientational data. Both the U.S. Pat. Nos. 4,849,692 and 4,945,305 patents relate to the use of magnetic fields to determine location in a three dimensional area despite the occasional and changing presence of metallic bodies which usually serve to distort the very field which is being relied upon for measurement. Both the U.S. Pat. Nos. 4,849,692 and 4,945,305 relate to locating a point in three dimensional space and are unrelated to either imaging or surgery.

U.S. Pat. No. 4,951,653 to Fry et al entitled "Ultrasonic Brain Lesioning System" discloses the use of ultrasound, CT (computerized axial tomography), or MRI (magnetic resonance imaging) in probing for site localization in conjunction with a skull fixation system. A precision ball provides linear and rotary positioning data by way of a cup fitting over a plurality of spheres and a linear encoder which interfaces with the cups. A bulky apparatus is utilized with a series of joystick type "precision balls" to direct an ultrasound signal through a cooling media to produce volume lesions in the brain at the site of identified brain tumors. The device is not utilized with open surgery, and the production of lesions is based upon the machine targeting of pre-existing tumors and the production of lesions without cutting the body.

U.S. Pat. No. 4,959,610 to Suzuki et al, entitled "Magnetic Resonance Apparatus" discloses details pertinent to NMR electromagnetic field atomic theory. U.S. Pat. No. 5,050,608 to Watanabe et al, entitled "System for indicating a Position to be Operated in a Patient's Body," discloses the use of an articulated probe as a control source for displaying a series of tomographical images on a cathode ray tube. This device assumes the orientation of the patient with respect to the device. If the patient moves, especially during surgery, the mechanical pointer may be pointing to a portion of the patient's anatomy such that the computer controls produce a tomographical image which is keyed to another portion of the patient's anatomy.

Further, since the Watanabe device includes four joints, a significant error is introduced in the resolution since the spatial Location of the pointer is dependent on the positions of the various angular displacement sensors at the joints of the articulated arm of the pointer. Further, the pointer is made collapsible so that it can be pushed toward the scalp to indicate an affected part in order for a surgeon to be enabled to make an incision. A solid tip can be pushed into the brain to indicate the depth of the tip into the brain while using the notches on the pointer to measure depth into the brain. This device is stated as being useful to assist in the initiation of surgery rather than assist during surgery, particularly since there is no provision to account for movement of the patient during the surgery.

U.S. Pat. No. 5,094,241 to Allen, entitled "Apparatus for Imaging the Anatomy," involves the placement of implants below the skin level and on the bones in order to key a patient to an imaging system. This method is utilized to account for problems in re-imaging for circumstances where significant amounts of time pass between a first and subsequent examinations. In such cases, a shift in viewing angle which might make a volume of interest appear larger or smaller compared to a subsequent examination, is corrected for by using the implants. The implants utilized must be of the type which will show up on a tomographic imaging system in order to register it to the images produced in a given examination.

U.S. Pat. No. 5,107,839 to Houdek et al and entitled "Computer Controlled Stereotaxic Radiotherapy System and Method," discloses a low frequency electromagnetic position detection means. The patient's head is repetitively position re located using a halo attached to the patient's head with skin piercing screws and which operates within a large multi-structured stereotaxic cage. The halo and cage would significantly interfere with surgery, and would be affected by the presence of metal surgical tools within the stereotaxic cage.

U.S. Pat. No. 4,791,934 to Brunnett, entitled "Computer Tomography Assisted Stereotactic Surgery System and Method" discloses a system using a multi-jointed referencing system. In the Brunette patent, a CT scan occurs at one location and is digitally stored in a computer. At a second location the patient is positioned in a digital radiographic imaging device utilized to produce a shadowgrahic image which is also stored. The shadowgraphic image is then registered with the scan image which may be accomplished visually on a video monitor on an operating table and "registered" in 3 dimensions with the CT data using shadowgraphic images shown on a display. The Brunette patent teaches that once the patient is "registered" the surgeon can then plan the best path of entry with a biopsy needle. The shadowgraphic image is formed with an X-ray device, thus presenting concerns about excess radioactive exposure of the patient.

Most of these systems are bulky, cumbersome, and generally more related to matching the coordinates of one system with those of another system. Each one presents an advancement in the art, but all fail to teach the construction of a system which joins the coordinate resolution of a physical three dimensional system with the two dimensional nature of non-invasive imaging.

SUMMARY OF THE INVENTION

The present invention enables stereotactic surgery with a minimal structure present in order to facilitate surgery yet with enhanced accuracy in stereotactic imaging assistance to the surgeon. This device and method is known as "frameless" stereotaxis system, and uses coordinate referencing between the CT or MRI scans and a stereotactic referencing system which uses an electromagnetically driven system to determine the location of a stylus.

Magnetic field distortion is reduced through the use of a low frequency magnetic field. One such system utilizing low frequency radiation is the "Flock of Birds™" system currently available from Ascension Technology Corporation of Burlington, Vt. The frame of reference through which this system operates is coordinate referenced to the coordinates of a composite image formed from a CT, MRI, or other system. Slice images from the CT, MRI, or other system scan are arranged and may be generated in two dimensional fashon in response to the position of a pointer as they are referenced to the orientation of a patient during an operation. As has been established in the literature, the precision and exactitude with which surgery can be performed is directly related to the surgeon's ability to pinpoint the tissue mass to be removed or cut. In the present device and method, registration of the scan images illustrating the lesion, with the physical position of the patient is performed by first synchronizing to two coordinate systems. Such synchronization can be performed in several ways, including the calibration of the stylus to several landmarks on the patient's anatomy.

The device and method of the invention also utilizes a transformation matrix which corrects for both angular displacement of the patient with respect to the "bird" system coordinates, and angular displacement of the visual image slice with respect to the angular displacement of the patient. The invention facilitates the use of peripheral devices such as the use of a "heads up" display, or other line of sight referencing structure.

DETAILED DESCRIPTION OF THE PREFERRED EMBODIMENT

The system of the present invention includes a system and method which correlates (1) a three dimensional magnetic field digitizer, (2) the anatomical features of a patient and (3) diagnostic images of the patient such as Computed Tomography (CT) and Magnetic Resonance Imaging (MRI). The explanation of the system can be best explained by initially referring to FIG. 1.

Figure 1:
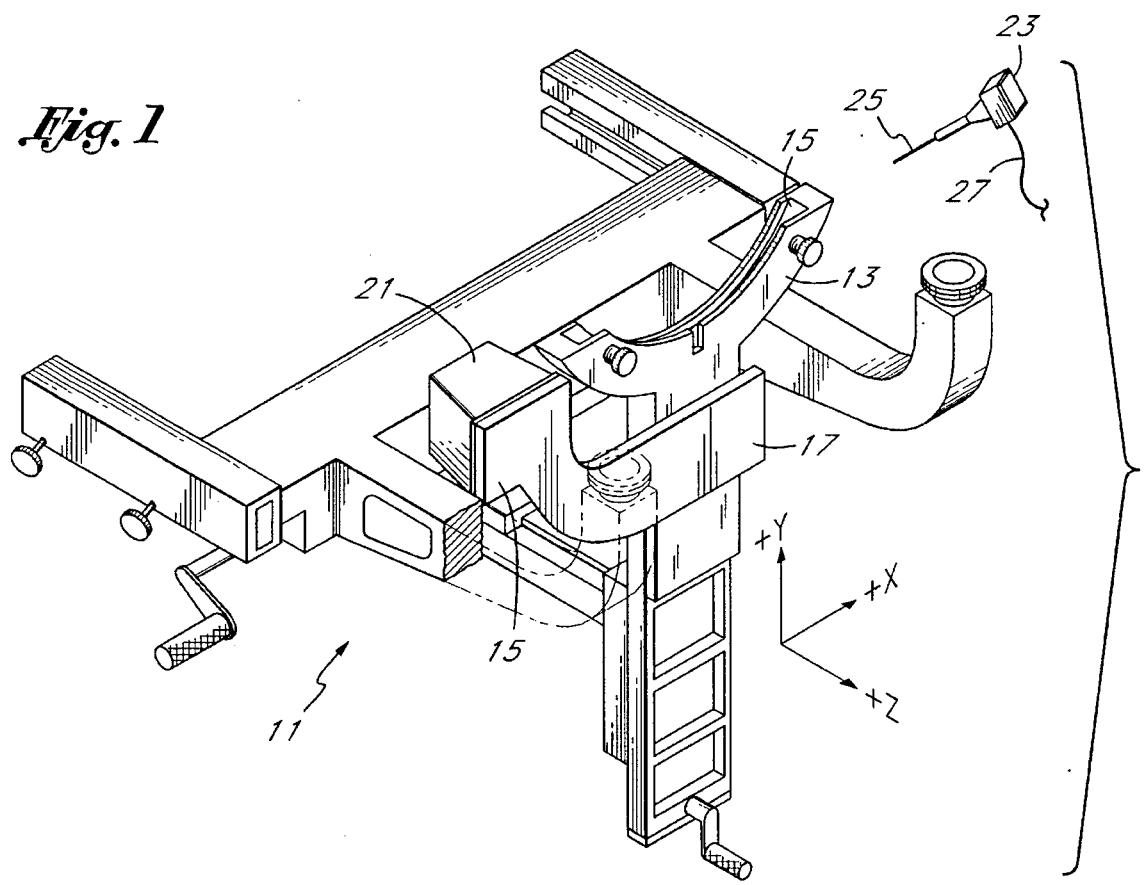
FIG. 1 is a perspective view of a standard Mayfield or Gardner headholder showing the positions of attachment for the electromagnetic source and the use of the electromagnetic receiver and stylus.

FIG. 1 is a perspective view of a standard Mayfield or Gardner headholder, hereinafter headholder 11, but with some of the head support structure removed for clarity. The perspective taken in FIG. 1 would best enable the surgeon to be seated at the lower right portion of FIG. 1. A "Y" shaped structure 13 includes a slot 15 at its upper portion to interfit with the head support structure which was removed for clarity.

Attached to this "Y" shaped structure 13 is a transmitter structural support 17 which is shown extending away from the "Y" shaped structure 13 to the left and curvingly upward. The transmitter structural support 17 terminates into a square shaped end 19. The square end 19 has a dimensions matching the base dimensions of an electromagnetic transmitter 21. Transmitter 21 is a frusto-pyramidal shaped box, and is supported by the transmitter structural support 17 in a manner to enable it to be supported as near as possible to the position occupied by the patient's head, as will be shown in FIG. 2.

Permanent mounting of the transmitter is desirable for a number of reasons. First, it will always bear the same relationship, during surgery, to the operating table, the headholder support 15 as well as the further headholder structural supports not shown in FIG. 1. Further, since most of the structure shown in FIG. 1 is ferromagnetic, tending to distort any magnetic field present, the constant position of the transmitter 21 will enable these distortions to be accounted for at one time, with out the necessity to re-calibrate each time the transmitter 21 is shifted.

Also shown in FIG. 1 is the electromagnetic receiver 23 and attached stylus 25. As will be shown, the point of reference in this system is the center of the electromagnetic receiver 23. However, since the center of the electromagnetic receiver 23 cannot be positioned immediately adjacent the structure to be measured, computational adjustments are performed to enable the referencing to be accomplished with respect to the tip of the stylus 25. Such adjustments are easily accomplished once the length of the stylus 25 is known. Also shown leading away from the electromagnetic receiver 23 is a lead 27, through which are passed signals which were received from the electromagnetic receiver 23. The lead 27 is connected to a computer (not shown in FIG. 2) in order that the position of the electromagnetic receiver 23 may be utilized to reference the relevant scan section, as will be shown.

In FIG. 1, the electromagnetic transmitter 21 and receiver 23 are part of a commercially available system known as the "Bird" Position and Orientation Measurement System, which is manufactured by Ascension Technology Corporation of Burlington, Vt. The "Y" shaped structure is part of a COMPASS™ Stereotactic Positioner which is commercially available from Stereotactic Medical Systems, Inc of Rochester, Minn. The use of the electromagnetic transmitter attached directly to a stereotactic positioner allows the coordinates being acquired by the "Bird" to be translated to the coordinate system of the stereotactic positioner because the orientation of the two coordinate systems remain in constant alignment. The value of this approach is that the stereotactic positioner, a proven tool for localizing surgical targets, acts to independently confirm the position reported by the "Bird" to verify that the positioning system is performing correctly. In doing so, the patient's head 31 is placed within the magnetic field produced by the electromagnetic transmitter 21, allowing coordinate determination, both with respect to the "Bird" and the COMPASS™ of specific anatomical references and that are also seen on CT or MR images. In doing so, calculations can be made to relate the location of the stylus to correlate the patient's anatomy to the diagnostic images.

Figure 2:
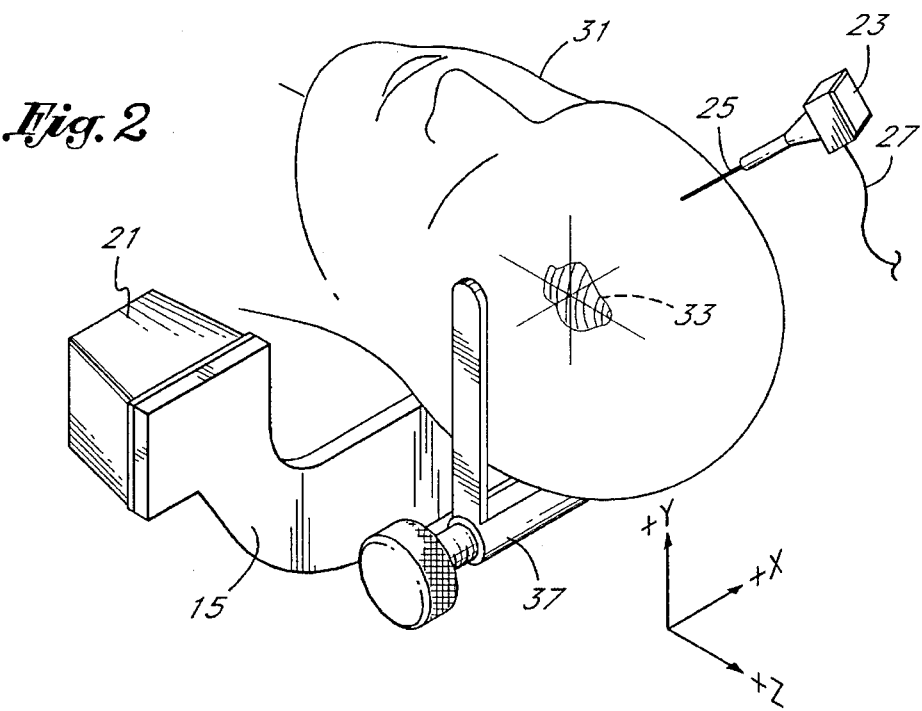
FIG. 2 is a perspective schematic view of the headholder of FIG. 1 with a patient, having a volumetric lesion, in operating position and the stylus employed.

Referring to FIG. 2, an enlarged view, taken from a position similar to that shown in FIG. 1, illustrates the position of the electromagnetic transmitter 21, headholder support 15, electromagnetic receiver 23 and stylus 25 with respect to a patient's head 31 having a volumetric lesion 33 shown at the approximate center of the patient's head 31. Also shown are additional head support structures 37 used to grasp and fix the position of the patient's head 31. Note the openness of the area about the patient's head 31 and the associated freedom with which surgery may be performed.

The importance of this "frameless" device in the surgical environment enables the surgeon to use this device as a guide to relate the surgical field to the diagnostic images helping him/her to better determine the location and margins of the legion. This is especially important when the lesion is adjacent to areas that are sensitive to surgical invasion.

The "Bird" tracking device, as it is presently commercially available, is a six degree of freedom measuring device which can be configured to simultaneously track the position and orientation of up to thirteen electromagnetic receivers 23 with a single electromagnetic transmitter 21.

Figure 3:
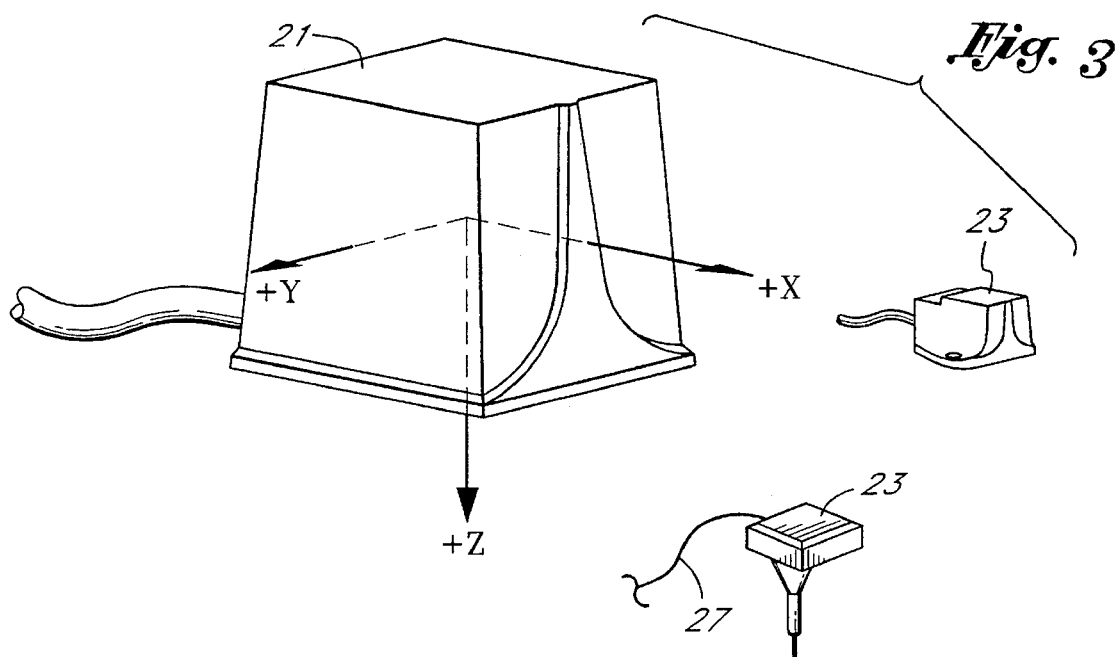
FIG. 3 is an expanded view of the electromagnetic transmitter and the electromagnetic receiver, without the stylus, and illustrating the coordinate system in which they operate.

Referring to FIG. 3, an enlarged view of the transmitter 21 and receiver 23 is illustrated. Within the transmitter 21, and shown partially in phantom is the center of the X, Y, and Z coordinate system with which the receiver 23 measures its spatial displacement. The positive Y direction is shown extending to the left and toward the observer, the positive X direction is shown extending to the right and toward the observer, while the positive Z direction is shown as being directed downwardly.

The orientation of the receiver 23 matches the orientation of the transmitter 21 in FIG. 3, and is shown in a parallel position. The spike design, and the frusto-pyramidal shape of the transmitter 21 assist in the ready identification of the orientation of the transmitter 21 with regard to its coordinate system shown in FIG. 3.

Each electromagnetic receiver 23 is capable of making from 10 to 144 measurements per second of its position and orientation when a electromagnetic receiver 23 is located within a finite, reasonably close distance from the electromagnetic transmitter 21. A pulsed direct current, or DC magnetic field enables the electromagnetic receivers 23 to determine position and orientation. From the measured magnetic field characteristics, each electromagnetic receiver 23 independently computes its position and orientation and makes this information available to a computer (not shown).

Each electromagnetic receiver 23 contains two independent serial interfaces, including a first for communications between the sensor and the computer, and a second for communications between itself and the other electromagnetic receivers 23, if necessary.

The proposed device and method of the present invention involves the use of the commercially available "Bird" device, also known as a magnetic field tracker and digitizer, which is modified for use in the operating room. The system and method of the present invention has as its function to gather three dimensional spatial information which is transferred to a host computer system wherein the digitized coordinates are transformed into surgical space coordinates. The position of the tip of the stylus 25 is displayed on CT or MRI slices or on three dimensionally rendered images from CT and/or MRI scans. Its purpose is to orient the surgeon by direct real-time comparison of the position of the stylus 25 tip in the surgical field with respect to the patient's anatomy defined by preoperative imaging. The advantage of this system over multi-jointed rigid digitizer systems is that the surgical pointer is connected to the interfacing modules by the highly flexible insulated lead 27 only. This is much less cumbersome to use during the course of a surgical procedure, than a multi-jointed arm connected to move about a single, anchored point.

Although technology for magnetic field digitizers has existed for some time, their use in the operating room has been rejected because of aberrant magnetic fields resulting from surgical tables, operating microscopes and electrical monitoring and diathermy equipment, emit distort the fields of the digitizers and render their results unpredictable, inaccurate and unreliable.

To deal with this problem, the device and method of the present invention employs a commercially available low frequency magnetic field digitizer, developed registration techniques, and a mechanical and software based method for determining and correcting for magnetic field distortion. The system and procedure of the present invention also provides a re-calibration feature, which allows the surgeon to translate the digitizers coordinate system based on touching of the pointer tip to a known point within the surgical field.

The device and method of the present invention also includes a low frequency magnetic digitizer unit which minimizes the interference artifact from aberrant fields created by metallic objects, as well as the electrical interference. To overcome this weakness, a technique using a three-dimensional distortion grid to help correct the distortion in the magnetic field was developed.

The magnetic distortion matrix is created utilizing a calibrated distortion phantom by the following method: First, coordinates for known points on the calibration phantom which is suspended within the surgical field are obtained by means of the stylus 25.

Figure 4:
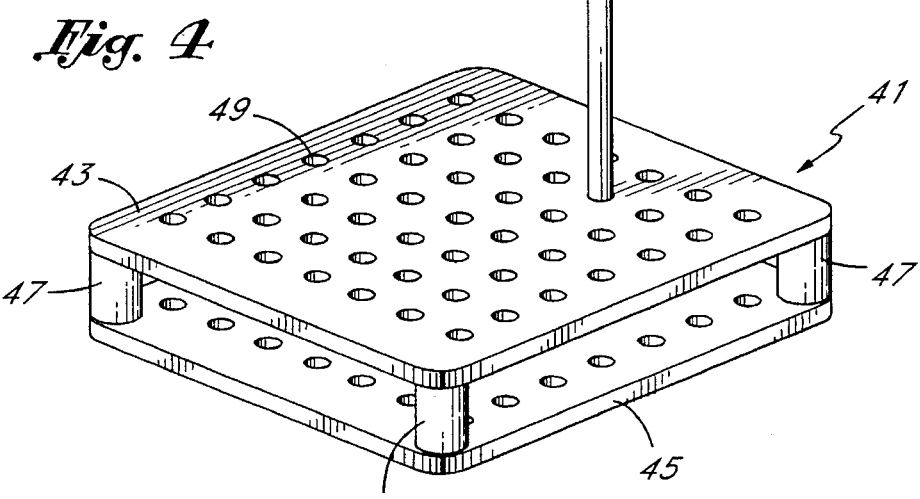
FIG. 4 illustrates the use of a calibration grid into which the electromagnetic receiver shown in Figures 1–3 is placed when calibrating the electromagnetic signal to account for non linearities in the electromagnetic field from a transmitter.

Referring to FIG. 4, a device utilized to assist in this process is shown. A calibration grid 41 consists of an upper plate 43 joined to and yet spaced from a lower plate 45 with a series of corner supports 47. The upper and lower plates 43 and 45 have a series of aligned holes 49 drilled therethrough. The axes of the holes are perpendicular to the parallel planes of the upper and lower plates 43 and 45. The diameter of the holes 49 match the diameter of a dipstick 51. However, the centers of the holes preferably have a three centimeter separation. The holes are arranged in a seven by seven (7×7) orientation. This orientation enables the representation of a group of six by six (6×6) two dimensionally square grids, the corners of the grids marked by the center point of the holes 49.

Further, the dipstick 51 is made to accept the stylus 25 of the electromagnetic receiver 23 and is actually attached into the end of the dipstick 51. The dipstick 51 is calibrated to provide seven levels of height. These seven levels of height, combined with the horizontal seven by seven orientation of holes 49 enable the projection of a volume of stacked three centimeter square grid cubes with the corners of the grid cubes defined by the seven by seven by seven coordinate points achievable with the calibration grid 41. Although the interfitting of the dipstick 51 with the calibration grid 41 occurs at the upper plate 43, it is the actual position of the electromagnetic receiver 23 in three dimensional space which results from the use of the calibration grid 41.

By recording the location of the electromagnetic receiver 23 at every level of the dipstick in every hole, the corner locations of the two hundred sixteen (216), three centimeter (3 cm) cubes located in the spaced defined by the calibration device are marked. This requires 7×7×7=343 measurements. Theoretically, the corners of each cube in the group of 216 cubes, or rather the potentials associated with the corners of the cubes, should each indicate a perfect cube, with each side of each cube being 3 cm in length. In reality, the cubes, due to distortions in their field potential, appear to be warped due to field distortions caused by ambient magnetic fields. The calibration device enables the database to correct for the warped nature of the cubes as actually measured, and enable the computer to identify a true point in space for the field strength at every point in space within the calibrated area.

The computer then calculates a distortion matrix and specific correction factors for many positions within the surgical work envelope. During the actual surgical procedure, these corrections factors are applied to the readings from the digitizer to correct for the non-uniformities of the field potential. Thus, coordinates for points measured in the surgical field are first modified by means of this distortion correction before being applied to the computer program for graphical representation of the position of the pointer within the CT and MRI data base.

The coordinate system inherent in CT and MRI examinations is equated to the coordinate system of the patient on the operating table and "Bird" magnetic field digitizer by two means. First, reference markers can be placed on the scald or into the outer surface of the patient's skull prior to the pre-surgical imaging. These are identified on the CT and/or MRI slice images as well as on the patient's head at surgery where their position can be identified to the computer by simply touching these skull markings with the end of the stylus 25. The computer can then calculate the transformation factors necessary to relate the coordinate system from CT and MRI to that of the "Bird" magnetic field digitizing pointer and thence to the surgical field, such as perhaps by an electronic overlay on a heads-up viewer or by an overlay onto a television camera image.

In addition, a contour map of the surface of the patient's head at surgery could be defined by laser scanner or by tracing lines over the surface of the patient's scalp by means of the electromagnetic receiver 23 and stylus 25. The end of the stylus can be stroked gently across the patient's face, skull, or other features in order to match the locality with the outer edge of the CT or MRI image. This can be accomplished by fitting the "contour map" generated from the stylus 25 to a "surface derived" contour map from CT and MRI imaging data detected by a manual or automatic intensity detection routine which traces using a cursor subsystem of the computer work station. A transformation matrix which transforms CT/MRI coordinates to the "Bird" magnetic field digitizer-surgical field coordinates is derived by means of contour matching or least-squares-fit routines.

The system of the present invention device comprises a commercially available unit low frequency magnetic field digitizer, a computer work station, a surgical pointer and distortion calibration phantom as well as software for distortion correction, coordinate transformation, real-time computer display of surgical pointer position and re-calibration. The end result is to display in real-time the position of the tip of the stylus 25 within a given work space, in this case the same body part at the time of surgery. This is done by computer display of a cursor in proper position on a corresponding CT or MRI slice or on a three dimensional volume rendering of the imaging data.

The purpose of the device and method of the present invention is to orient the surgeon as to the three dimensional position of points, or a volume when called for, within the surgical field with respect to the preoperative imaging data base. For example, such a device could help the surgeon identify the plane between tumor and non-cancerous tissue to allow more complete, safer and more well defined tumor removals. The system could alert surgeons to the proximity of important imaging-defined anatomical and vascular structures which must be preserved. In addition, such a device would allow rapid measurements from known landmarks as may be important in plastic and reconstructive or orthopedic surgery. Finally the device and method of the present invention, with appropriate interfacing, could be used to orient surgeons during endoscopic surgery.

Figure 5:
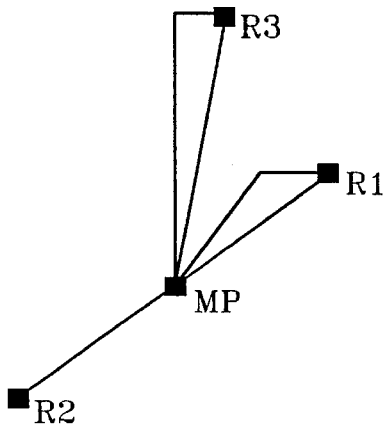
FIG. 5 is a graphical representation of the cartesian coordinate system utilized in conjunction with the present invention, and the angular displacement values $\beta$, $\alpha$, and $\gamma$, associated with rotation about the X, Y, and Z axes, respectively.

The major advantage of the proposed device over multijointed digitizer and robotic systems presently being considered is that it is connected by means of a relatively thin, highly flexible cord, namely lead 27 that does not present the cumbersome mechanical constraints of the multi-jointed arm. Properly shielded, lead 27 can assume almost any reasonable length, and its path from the magnetic field digitizer to the surgeon's hand can follow whatever circuitous route necessary for the surgeon's comfort, including over the shoulder, hanging from the headholder 11, or suspended from above. Correlating Anatomy and Images To correlate the patient's anatomy requires a minimum of three (3) points of reference common to the patient and the corresponding images, since three points determine a plane. Once the reference points have been isolated, a transformation matrix can be generated to transform the coordinate system of the "Bird" digitizer to the scan coordinate system, such as a CT coordinate system. Referring to FIG. 5, a schematic representation of the computation of the midpoint MP from a series of reference points R1, R2, and R3 in space, is shown. The midpoint MP has x, y, and z coordinates which are averages of the x, y, and z coordinates of the reference points R1, R2, and R3.

The reference points could be derived by insertion of the probe into the patient's ear cartilage or auditory canals to get the first two points, with the third point identified by placing the stylus at the bridge of the nose. These points give a fairly wide x, y, and z spacing and should result in a more stable midpoint MP than would occur if two or more of the points were more closely located.

The CT coordinate system is usually defined to have the X and Y origin at the center of the image slice and a displacement along the Z direction on the table for determining the Z value. However, for a video slice, the default coordinate system usually has an origin point at the upper left portion of the screen, and positive X displacement across the screen from left to right, and positive Y displacement downwardly across the screen from top to bottom. For instance, a 512 pixel X 512 pixel image would have its center at 256, 256 (measured in pixels). Multiplying the difference between the X/Y pixel location of a reference point or target point and the 256, 256 origin coordinate determines the X and Y coordinate in the CT system (the CT system having 0, 0 at its center). Knowing the CT table position for the image of interest determines the Z value for the coordinate.

In the commercially available "Bird" device, its coordinate system contains an origin located near the center of the source, namely electromagnetic transmitter 21. The positive Z axis projects out the bottom of the electromagnetic transmitter 21. As was shown in FIG. 3, the positive X axis projects out the side opposite the power cord and the Y axis projects up when looking into the Z axis at the bottom of the transmitter 21 with the power cord extending away from the transmitter 21 to the left. This coordinate system is a right handed coordinate system.

In determining the CT reference marks with the system and method of the present invention, the user reviews all of the available CT images to isolate three reference points for each image. On each image, one should be located on the left, one on the right and one anteriorly. Once these reference points have been located, the user displays each reference image and places a cross-hair cursor over the desired point to select it and store the coordinates for this point. This is done for each of the reference points.

The variables for each of the reference points are defined for later discussion, and are based upon a CT coordinate system discussed. The coordinate references are given in millimeters, and are with respect to the center of the CT reference scan, and are defined as follows:

1. Right CT reference point—CT1
   CT1x—The x coordinate of the first CT reference point.
   CT1y—The y coordinate of the first CT reference point.
   CT1z—The z coordinate of the first CT reference point.
2. Left CT reference point—CT2
   CT2x—The x coordinate of the second CT reference point.
   CT2y—The y coordinate of the second CT reference point.
   CT2z—The z coordinate of the second CT reference point.
3. Anterior CT reference point CT3
   CT3x—The x coordinate of the third CT reference point.
   CT3y—The y coordinate of the third CT reference point.
   CT3z—The z coordinate of the third CT reference point.

Again, remember that the CT reference points are defined for the CT system, a system which has the X and Y origin coordinates at the center of the scans.

In determining the "Bird" Reference Marks, the operator locates the same corresponding points on the patient which were selected on the CT images. The program will first display CT1 and ask the user to touch the corresponding point on the patient. By using a triggering foot switch, the surgeon or surgical worker can leave his hands free for surgical manipulation, and also eliminate the need for severe sterilization on the switch, since he need not touch it with the hands. With such a switch, the "Bird" digitizer coordinate for this point is entered into the computer for the right reference point. The overall system and method of the present invention has been referred to as the Regulus system. For this reason, a portion of the variables are given using this designation. This is repeated for the other two reference points. The reference dimensions are in millimeters. The variables for each of the reference points are as follows:

1. Right Regulus Bird reference point—RG1
   RG1x—The x coordinate of the first reference point.
   RG1y—The y coordinate of the first reference point.
   RG1z—The z coordinate of the first reference point.
2. Left Regulus Bird reference point—RG2
   RG2x—The x coordinate of the second reference point.
   RG2y—The y coordinate of the second reference point.
   RG2z—The z coordinate of the second reference point.
3. Anterior Regulus Bird reference point—RG3
   RG3x—The x coordinate of the third reference point.

RG3y—The y coordinate of the third reference point.
RG3z—The z coordinate of the third reference point.

A transformation matrix is calculated as a mathematically convenient way of manipulating the coordinate systems to account for angular displacements of the coordinate systems with respect to each other. Failure to use such a transformation matrix would result in the necessity to have a set of three difference values for each point in space to account for all of the changes due to the difference in the two coordinate systems, especially since angular displacement affects the difference at points in one end of the system differently than points in another portion of the system.

Figure 6:
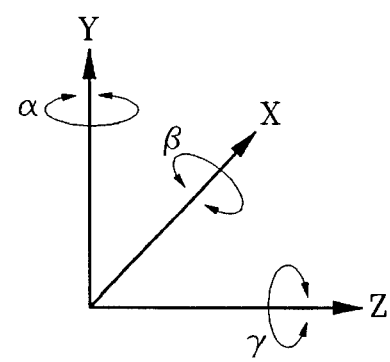
FIG. 6 illustrates the computation of a midpoint MP, utilizing the reference points R1, R2, and R3.

To correlate the patient's anatomy to the images requires a determination of how the patient is oriented within each of the two coordinate systems. Referring to FIG. 6 and using the reference points, the rotation about X ($\beta$), the rotation about Y ($\alpha$) and the ration about Z ($\gamma$) are calculated to determine how the patient is oriented in each of the coordinate systems.

Equations 1–3 shown below are the generic equations determine the location of the midpoint between the first and second reference points for either the CT or Regulus coordinate systems. In the following equations, MP represents the midpoint coordinates. R1 represents the coordinates of the first reference point. R2 represents the coordinates of the second reference point. Each of the coordinates are expressed in mm.

MPx (R1x–R2x)/2.0  Eq. 1

MPy (R1y–R2y)/2.0  Eq. 2

MPz (R1z–R2z)/2.0  Eq. 3

Equations 4–6 are the general formulas for determining the alpha, beta and gamma tilts of the patient sitting into either the Bird or CT coordinate systems in accord with that shown in FIG. 5. By definition, Beta is the rotation about the X axis, alpha is the rotation about the y axis, and gamma is the rotation about the z axis. The units for rotation are expressed in degrees.

Equation 4: Calculating Beta $$\beta = \frac{R3z - MPz}{\sqrt{(R3x - MPx)^2 + (R3y - MPy)^2 + (R3z - MPz)^2}}$$

Equation 5: Calculating Alpha $$\alpha = \frac{R1x - MPx}{\sqrt{(R1x - MPx)^2 + (R1y - MPy)^2 + (R1z - MPz)^2}}$$

Equation 6: Calculating Gamma $$\gamma = \frac{R1y - MPy}{\sqrt{(R1x - MPx)^2 + (R1y - MPy)^2 + (R1z - MPz)^2}}$$

Applying the above equations to both the CT reference points and the Bird reference points we calculate the alpha, beta and gamma rotations for both the CT and Regulus coordinate systems. Equations 7–12 are the actual equations used for calculating the specific rotations.

Equation 7: Beta $$\beta CT = \frac{CT3z - CTMPz}{\sqrt{(CT3x - CTMPx)^2 + (CT3y - CTMPy)^2 + (CT3z - CTMPz)^2}}$$

Equation 8: Alpha CT $$\alpha CT = \frac{CT1z - CTMPz}{\sqrt{(CT1x - CTMPx)^2 + (CT1y - CTMPy)^2 + (CT1z - CTMPz)^2}}$$

Equation 9: Gamma CT $$\gamma CT = \frac{CT1y - CTMPy}{\sqrt{(CT1x - CTMPx)^2 + (CT1y - CTMPy)^2 + (CT1z - CTMPz)^2}}$$

Equation 10: Beta Bird $$\beta RG = \frac{RG3z - RGMPz}{\sqrt{(RG3x - RGMPx)^2 + (RG3y - RGMPy)^2 + (RG3z - RGMPz)^2}}$$

Equation 11: Alpha Bird $$\alpha RG = \frac{RG1z - RGMPz}{\sqrt{(RG1x - RGMPx)^2 + (RG1y - RGMPy)^2 + (RG1z - RGMPz)^2}}$$

Equation 12: Gamma Bird $$\gamma RG = \frac{RG1z - RGMPz}{\sqrt{(RG1x - RGMPx)^2 + (RG1y - RGMPy)^2 + (RG1z - RGMPz)^2}}$$

In Equations 7–12:
  CT1x is the X coordinate for CT reference point 1.
  CT1y is the Y coordinate for CT reference point 1.
  CT1z is the Z coordinate for CT reference point 1.
  CT2x is the X coordinate for CT reference point 2.
  CT2y is the Y coordinate for CT reference point 2.
  CT2z is the Z coordinate for CT reference point 2.
  CTMPx=(CT1x–CT2x)/2.0
  CTMPy=(CT1y–CT2y)/2.0
  CTMPz=(CT1z–CT2z)/2.0
  CT3x is the X coordinate for CT reference point 3.
  CT3y is the Y coordinate for CT reference point 3.
  CT3z is the Z coordinate for CT reference point 3.
  RG1x is the X coordinate for Regulus reference point 1.
  RG1y is the Y coordinate for Regulus reference point 1.
  RG1z is the Z coordinate for Regulus reference point 1.
  RG2x is the X coordinate for Regulus reference point 2.
  RG2y is the Y coordinate for Regulus reference point 2.

$$\begin{bmatrix} 1 & 0 & 0 & 0 \\ 0 & 1 & 0 & 0 \\ 0 & 0 & 1 & 0 \\ -RGMPx & -RGMPy & -RGMPz & 1 \end{bmatrix} \begin{bmatrix} \cos\gamma RG & \sin\gamma RG & 0 & 0 \\ -\sin\gamma RG & \cos\gamma RG & 0 & 0 \\ 0 & 0 & 1 & 0 \\ 0 & 0 & 0 & 1 \end{bmatrix} \begin{bmatrix} 1 & 0 & 0 & 0 \\ 0 & \cos\beta RG & \sin\beta RG & 0 \\ 0 & -\sin\beta RG & \cos\beta RG & 0 \\ 0 & 0 & 0 & 1 \end{bmatrix} \begin{bmatrix} \cos\alpha RG & 0 & -\sin\alpha RG & 0 \\ 0 & 1 & 0 & 0 \\ \sin\alpha RG & 0 & \cos\alpha RG & 0 \\ 0 & 0 & 0 & 1 \end{bmatrix} = M1$$

RG2z is the Z coordinate for Regulus reference point 2.
  RGMPx=(RG1x–RG2x)/2.0
  RGMPy=(RG1y–RG2y)/2.0
  RGMPz=(RG1z–RG2z)/2.0
  RG3x is the X coordinate for Regulus reference point 3.
  RG3y is the Y coordinate for Regulus reference point 3.
  RG3z is the Z coordinate for Regulus reference point 3.

Please note that all of the coordinates are in millimeters.

There are several common anatomical reference points which may be utilized to accommodate the physical interrelationship to be established between the Regulus and CT images. The requirement is that the reference points selected with the Regulus must be available on the CT images in order to translate the Regulus coordinates into the CT coordinates. One example of common reference points would be the use of the right external auditory canal as reference point 1, the left external auditory canal as reference point 2 and the nasion as reference point 3. The user would select each of these reference points on the CT images and point to these points on the patient with the stylus 25.

If the inventive system and method of the present invention is being used in conjunction with the COMPASS™ stereotactic positioner, then known points on the stereotactic headholder 11 can serve to provide the reference points. These points have known coordinates with respect to the CT data. The stylus 25 of the Regulus system is used to touch each of these points to register the Regulus coordinate for the three reference points.

Similarly, the Regulus Coordinates can be coordinated to the CT coordinates. To convert a point from the Bird coordinate system to that of the CT coordinate requires a transformation matrix M1. The midpoint between reference points RG1 and RG2 serves as the origin of the patient coordinate system. Therefore, the first step is to translate the Midpoint (MP) to (0,0,0) followed by the rotations of the head in the Bird coordinate system.

Once this transformation is utilized, the Bird coordinate system is aligned with the patient coordinate system based on the three selected anatomical reference points. Now using this information, the patient coordinate system needs to be rotated to fit the CT coordinate system and finally translated into the coordinate system of the CT images. The following equation generates a matrix M2, used to align the patient coordinate system to the CT coordinate system.

$$\begin{bmatrix} \cos\alpha CT & 0 & -\sin\alpha CT & 0 \\ 0 & 1 & 0 & 0 \\ \sin\alpha CT & 0 & \cos\alpha RG & 0 \\ 0 & 0 & 0 & 1 \end{bmatrix} \begin{bmatrix} 1 & 0 & 0 & 0 \\ 0 & \cos\beta CT & \sin\beta CT & 0 \\ 0 & -\sin\beta CT & \cos\beta CT & 0 \\ 0 & 0 & 0 & 1 \end{bmatrix} \begin{bmatrix} \cos\gamma CT & \sin\gamma CT & 0 & 0 \\ -\sin\gamma CT & \cos\gamma CT & 0 & 0 \\ 0 & 0 & 1 & 0 \\ 0 & 0 & 0 & 1 \end{bmatrix} = M2 \qquad \text{Equation 14}$$

Matrix M1 is multiplied to M2 to generate matrix M3

$$M1 \times M2 = M3 \qquad \text{Equation 15}$$

Finally, the translation to the CT coordinate system is calculated.

$$M3x \begin{bmatrix} 1 & 0 & 0 & 0 \\ 0 & 1 & 0 & 0 \\ 0 & 0 & 1 & 0 \\ CYMPx & CTMPy & CTMPz & 1 \end{bmatrix} = \text{Transmatrix} \qquad \text{Equation 16}$$

As has been previously described, a calibration grid 41 is utilized to physically position the electromagnetic receiver 23 in 343 positions in order that the three orthogonal field strengths be measured for each position. Also as previously stated the field strengths will be distorted or "warped" due to the influence of other ferromagnetic structures present along with the "Bird" digitizing device. Following is the specific technique using the particular calibration grid 41 having a 7×7×7 orientation. It is understood that other methods can be used, and indeed other models which may be based upon a calibration grid having dimensions other than those recited for calibration grid 41.

As previously explained with regard to FIG. 4, the three dimensional distortion calibration device, or calibration grid 41 has two parallel plates 43 and 45 with a grid of holes 49 arranged in a 7×7 configuration spaced 3 cm apart. The dipstick 51, which is inserted into the holes, has seven marks at three centimeter intervals along its length, and accepts the stylus 25 attached at the end of the dipstick 51. By recording the location of the sensor in the stylus at every level of the dipstick in every hole, we have marked the 343 corner locations of the 216 three centimeter square cubes located in the spaced defined by the calibration device.

The distortion factors can be calculated in a number of steps. The first step is to acquire a distortion data base. Using the calibration grid 41, the dipstick 51 is inserted into hole "0" with the first measuring line on the dipstick 51 flush with the upper grid plate 43. The field reading for this location of the electromagnetic sensor 23 on the stylus 25 is stored. The dipstick 51 is advanced to the second measuring line on the dipstick 51 and the location recorded. This procedure is repeated for all of the seven lines of the dipstick. The dipstick is then placed into hole "1" and the location for each measuring line of the dipstick 51 is again recorded. This process is repeated for every hole of the calibration grid 41.

Next, the calibration database is translated and rotated so that the calibration data base is re-aligned to be located at the origin of the "Bird" digitizing source's electromagnetic transmitter 21 and oriented in the same direction as the "Bird" coordinate axes which were previously discussed.

Third, and based upon the actual values for the corners of each of the three centimeter cubes whose corners are occupied by the electromagnetic receiver 23, a theoretical value, also known as a warping value is calculated for each corner.

Fourth, a warping value is applied for every point that is acquired from the placement of the electromagnetic receiver 23 in the 343 positions over the calibration grid 41. Each one of the three centimeter cubes associated with the 343 points recorded in the calibration activity is isolated and a cube warping value is determined which is calculated based upon the warping values at each of the eight corners of each calibration cube. Also taken to account is the distance of the point to each of the corners. Following are a set of equations which will facilitate the warping calculations just described.

Figure 7:
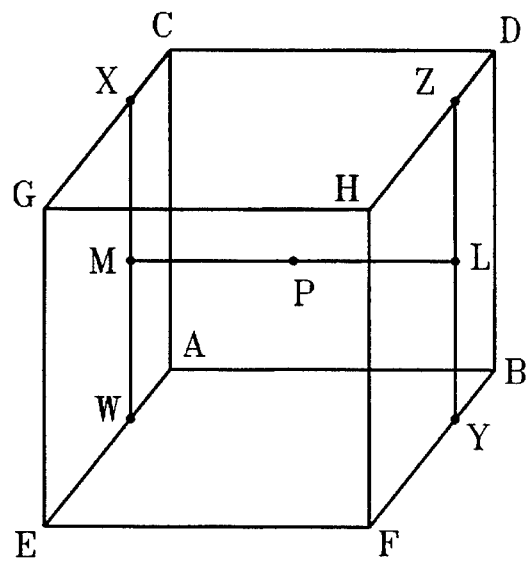
FIG. 7 illustrates the cubic reference points utilized in the computation of warp correction.

The following equations 17–20 enable the calculation of the coordinates for the intermediate edge points of each cube. Referring to FIG. 7, a diagram of the cubic points for which calculations follow is illustrated.

$$Wi = Ai + ((Ei - Ai) \times ((Pz - Az)/(Ez - Az))) \qquad \text{Eq. 17}$$

$$Xi = Ci + ((Gi - Ci) \times ((Pz - Cz)/(Gz - Cz))) \qquad \text{Eq. 18}$$

$$Yi = Bi + ((Fi - Bi) \times ((Pz - Bz)/(Fz - Bz))) \qquad \text{Eq. 19}$$

$$Zi = Di + ((Hi - Di) \times ((Pz - Dz)/(Hz - Dz))) \qquad \text{Eq. 20}$$

Where Ai, Bi, Ci, Di, Ei, Fi, Gi, and Hi represent the coordinates of the corners of a cube, and where i represents the x, y, or z coordinate value. The units used in equations 17–20 are in millimeters. The resulting distortion file is made up of 343 cubes. When correcting a point for magnetic distortion, a determination is made as to which of these cubes the point is within. Once this is determined, a series of intermediate values are computed, which are the intermediate values shown in FIG. 7. The intermediate values are immediately seen for the example cube shown in FIG. 7, but the equations necessary to carry out the computations for 343 cubes require a greater degree of formalism. The variables in equations 17–20 are defined as follows:

Wi—represents the coordinates of a linearly interpolated point between points A and E, where i represents the x, y, or z coordinate values.

Xi—represents the coordinates of a linearly interpolated point between points C and G, where i represents the x, y, or z coordinate values.

Yi—represents the coordinates of a linearly interpolated point between points B and F, where i represents the x, y, or z coordinate values.

Zi—represents the coordinates of a linearly interpolated point between points D and H, where i represents the x, y, or z coordinate value.

Once the intermediate values Wi, Xi, Yi, and Zi are computed, and as are shown in FIG. 7, a value intermediate to the Wi and Xi values, namely Mi is needed. Similarly a value intermediate to the Wi and Xi values, namely Li is needed. The equations 21 and 22 set forth the relationships enabling the Mi and Li values to be calculated. The L and M portions of the unit cube are shown in FIG. 7.

$$Mi = Wi + ((Xi - Wi) \times ((Py - Wy)/(Xy - Wy))) \qquad \text{Eq. 21}$$

$$Li = Yi + ((Zi - Yi) \times ((Py - Yy)/(Zy - Yy))) \qquad \text{Eq. 22}$$

Here, Mi—represents the coordinates of a linearly interpolated point between points W and X, where i represents the x, y, or z coordinate value, and Li—represents the coordinates of a linearly interpolated point between points Y and Z, where i represents the x, y, or z coordinate value.

The warp factor for each of the corners need to be calculated for each coordinate. Equations 23–25 are determining the warp factor for corner "A". This calculation needs to be repeated for each corner to produce BWi, CWi, DWi, EWi, FWi, GWi, and HWi (where i represents the x, y or z warp factors for each of the corners).

$$AWx = ATx - ARx \qquad \text{Eq. 23}$$

$$AWy = ATy - ARy \qquad \text{Eq. 24}$$

$$AWz = ATz - ARz \qquad \text{Eq. 25}$$

Definition of Variables for Equations 23–25:

AWx—The x warp factor at corner A of the warp cube.

AWy—The y warp factor at corner A of the warp cube.

AWz—The z warp factor at corner A of the warp cube.

ATx—The theoretical or desired x coordinate for corner A.

ATy—The theoretical or desired y coordinate for corner A.

ATz—The theoretical or desired z coordinate for corner A.

ARx—The Regulus x coordinate for corner A of the warped cube.

ARy—The Regulus y coordinate for corner A of the warped cube.

ARz—The Regulus z coordinate for corner A of the warped cube.

Equations 26–29 determine the warp factor at the intermediate edge points.

$$WWi = AWi + ((EWi - AWi) \times ((Pz - ARz)/(ERz - ARz)))\qquad \text{Eq. 26.}$$

$$XWi = CWi + ((GWi - CWi) \times ((Pz - CRz)/(GRz - CRz)))\qquad \text{Eq. 27.}$$

$$YWi = BWi + ((FWi - BWi) \times ((Pz - BRz)/(FRz - BRz)))\qquad \text{Eq. 28.}$$

$$ZWi = DWi + ((HWi - DWi) \times ((Pz - DRz)/(HRz - DRz)))\qquad \text{Eq. 29.}$$

Definitions of variables in equations 26–29:

WWi—The warp factor for each coordinate at point W (where i represents x, y or z)

XWi—The warp factor for each coordinate at point X (where i represents x, y or z)

YWi—The warp factor for each coordinate at point Y (where i represents x, y or z)

ZWi—The warp factor for each coordinate at point Z (where i represents x, y or z)

Equations 30 and 31 determine the warp factor for the intermediate side points.

$$MWi = WWi + ((XWi - WWi) \times ((Py - Wy)/(Xy - Wy)))\qquad \text{Eq. 30.}$$

$$LWi = YWi + ((ZWi - YWi) \times ((Py - Yy)/(Xy - Yy)))\qquad \text{Eq. 31.}$$

Lastly, equation 32 determines the warp factor for the point at the center of each cube is located. This point is shown simply as "P" in FIG. 7.

$$PWi = MWi + ((LWi - MWi) \times ((Px - Mx)/(Lx - Mx)))\qquad \text{EQ. 30.}$$

Here, the term PWi—is the warp factor for each of the x, y, or z coordinates for each of the points obtained during calibration. During surgery, as the "Bird" system picks up points in space using the electromagnetic receiver 23, the "warped" coordinates detected by the "Bird" system will be converted to accurate x, y, and z coordinates before being utilized to identify corresponding points and slices on the CT scans. Alternatively, this correction is used before displacing an indicator in a computer generated perspective image to provide to the surgeon a three dimensional location of the stylus 25 with respect to a proper scan image.

Figure 8:
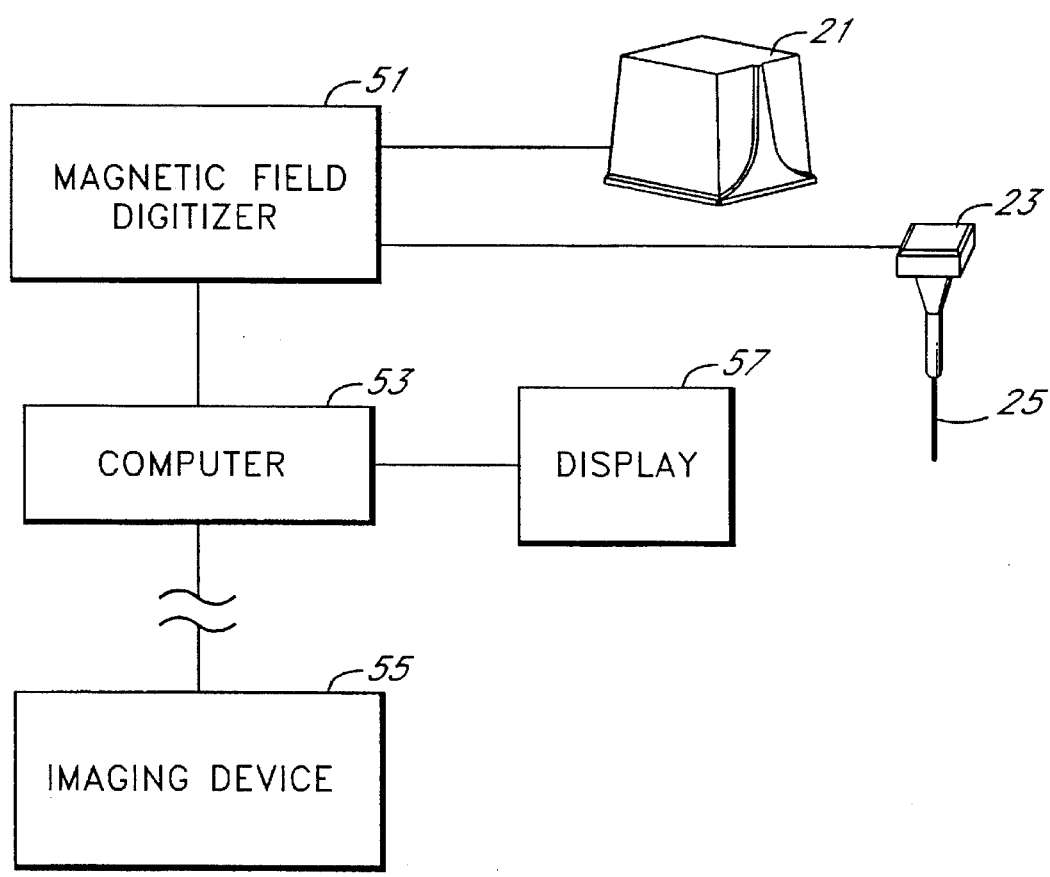
FIG. 8 is a schematic representation of one possible system configuration in which the method and system of the present invention can be practiced.

In commercial practice, a system can be formulated using a single unit, or several sub-units. The choice of the number and configuration of electronic units utilized in the system and method of the present invention will probably depend more upon commercial expediency than any other factor. Referring to FIG. 8, one possible schematic for the device of the invention is shown. In this configuration, a separate device, a Magnetic Field Digitizer 51 is shown connected to the electromagnetic transmitter 21 and the electromagnetic receiver 23. Also shown connected to the electromagnetic receiver 23 is the stylus 25.

In the configuration of FIG. 8, the Magnetic Field Digitizer 51 is utilized to provide the three dimensional location data to a computer 53. In this configuration, the computational iterations to form the warp factors will most likely be executed within the computer 53. Such would be especially true where the computational ability of the Magnetic Field Digitizer 51 were limited, or where a minimum complexity Magnetic Field Digitizer 51 was the most economically feasible.

In this configuration, the computer 53 would be alerted to operate in test mode before the digitization of the positions of the electromagnetic receiver 23. Consequently, and during operation, the Magnetic Field Digitizer 51 would transmit raw coordinate data into the computer 53, with the computer 53 then making the warp corrections based upon the data gathered during the calibration step.

The computer 53 is also, at times, connected to an imaging device 55, such as a CT or MRI scanner. The connection between the computer 53 and the imaging device 55 is shown in broken line, since the connection need not be constant. For example, an MRI scan can be performed earlier in time, and then the data obtained in the MRI scan can be transmitted to the computer 53 later in time. The transmission can be accomplished by physical transfer of the data, for example by diskette, computer tape, or portable hard drive. The transmission of data can also be accomplished by modem; hard wire transfer such as by a serial or parallel port; or even by packet, spread spectrum or digital radio communications.

Connected to the computer 53 is a display 57. Display 57 can be a screen of any type, and it is contemplated that the screens may be cathode ray tube, liquid crystal display, virtual reality, heads up display, or projection onto a surface, to name a few. The display 57 may combine a visual representation of the scan information in combination with a visual observation of the surgical field. Such a device has been referred to as a "heads up" display, and typically allows the surgeon to simultaneously view an image from the imaging device along with an image from the surgical field. Usually the image from the imaging device is somewhat transparently overlaid over a solid image of the surgical field, but either image can be made transparent.

The display 57 may physically stand alone, or may be included in a device to be worn by the surgeon. Video monitors have been incorporated into head gear, eye gear, and the like, and it is anticipated that display 57 may also be a video monitor similarly incorporated into such support structures. Such monitors can also be optical and involve various transformations to highlight the problem areas. Further, it is anticipated that the instant system may be incorporated for use where the three dimensional locator, the electromagnetic receiver 23 and stylus 25, are utilized simultaneously with the acquisition of the scan image. Such use could incorporate a direct calibration scheme for the stylus 25 and a calibration refresh procedure to periodically re-calibrate the location of the electromagnetic receiver 23 and stylus 25. Such refreshing re-calibration would be particularly useful where ferromagnetic structures are brought into the three dimensional measurement space utilized by the electromagnetic receiver 23 and electromagnetic transmitter 21, since the introduction and movement of such ferromagnetic structures may alter the initially determined warp calculations. Such interactive scan acquisition with positional location would also account for shifts in the tissue mass due to removal of damaged tissue. Such a refresh procedure could use a calibration grid or a few selected known common points.

Further, the scan acquisition activity and the positional location activity could be controlled in a way that their performance would be based upon need. For example, since the imaging activity is typically electromagnetic, its occurrence could be timed to occur during times when the positional location activity was not occurring. Since the positional location system is ideally a low frequency system, filters could be utilized to separate the cross effects between the two fields if any reduced resolution from simultaneous operations could be tolerated. If not, the system could be designed to trigger the system undergoing the greatest change per unit time. If significant changes were being made to the tissue, a controller might increase the ratio of refresh cycles in the imaging scan to the ratio of refresh cycles for updating the position of the stylus 25. Likewise, where the stylus 25 significantly changed position, a controller might decrease the ratio of refresh cycles in the imaging scan to the ratio of refresh cycles for updating the position of the stylus 25.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A locating device for use with sterotactic device comprising:
    electromagnetic position indicating means for generating an output position signal identifying the location of a reference position with respect to a surgical field, and wherein said electromagnetic position indicating means further comprises:
    an electromagnetic transmitter having an input;
    an electromagnetic receiver having an output;
    a magnetic field digitizer having an input connected to said output of said electromagnetic receiver and a first output connected to said input of said electromagnetic transmitter, and a second output for outputting a position signal;
    a computer having an input connected to said second output of said magnetic field digitizer, a data input, and a display output; and
    a display having an input connected to said display output of said computer;
    an imaging scan display system having an input connected to receive said output position signal from said electromagnetic position indicating means and adapted to display a scan image associated with the three dimensional position of said reference position in said surgical field; and
    a head holder for performing cranial surgery and wherein said head holder supports said electromagnetic transmitter.

2. A locating device for use with a stereotactic device comprising:
    electromagnetic position indicating means for generating an output position signal identifying the location of a reference position with respect to a surgical field, and wherein said electromagnetic position indicating means further comprises:
    electromagnetic transmitter means for transmitting electromagnetic energy;
    an electromagnetic transmitter receiver means for receiving electromagnetic energy;
    magnetic field digitization means having an input connected to said electromagnetic receiver means, a first output connected to said electromagnetic transmitter means, and a second output for outputting a position signal;
    computer means for identifying and transmitting a scan image associated with the position of said reference position and for correcting error associated with said position signal, and having an input connected to said second output of said magnetic field digitization means, a data input, and a display output and
    display means for receiving said transmitted scan lines and displaying said scan image and having an input connected to said display output of said computer means; and
    an imaging scan display system having an input connected to receive said output position signal from said electromagnetic position indicating mean and adapted to display a scan image associated with a three dimensional position of said reference position in said surgical field.

3. A locating device for use with a stereotatic device comprising:
    electromagnetic position indicating means for generating an output position signal identifying the location of a reference position with respect to a surgical field, and wherein said electromagnetic position indicating means further comprises:
    electromagnetic transmitter means for transmitting electromagnetic energy;
    an electromagnetic receiver mean for receiving electromagnetic energy;
    magnetic field digitization means having an input connected to said electromagnetic receiver means, a first output connected to said electromagnetic transmitter means, and a second output for outputting a position signal;
    computer means for identifying and transmitting a scan image associated with the position of said reference position and for computing a midpoint reference base upon at least three reference positions and at least three points on scan images, each point associated with the position of an associated said reference position; and having an input connected to said second output of said magnetic field digitization means, a data input and a display output; and
    display means for receiving said transmitted scan image and displaying said scan image and having an input connected to said display output of said computer means; and
    an imaging scan display system having an input connected to receive said output position signal from said electromagnetic position indicating means and adapted to display a scan image associated with a three dimensional position of said reference position in said surgical field.

4. A locating device for use with a stereotatic device comprising:
    electromagnetic position indicating means for generating an output position signal identifying the location of a reference position with respect to a surgical field, and wherein said electromagnetic position indicating means further comprises:
    electromagnetic transmitter means for transmitting electromagnetic energy;
    an electromagnetic receiver means for receiving electromagnetic energy;
    magnetic field digitization means having an input connected to said electromagnetic receiver means, a first output connected to said electromagnetic transmitter means, and a second output for outputting a position signal;
    computer means for identifying and transmitting a scan image associated with the position of said reference position and for correcting error associated with a position of said electromagnetic receiver means; and having an input connected to said second input of said magnetic field digitization means, a data input, and a display output; and display means for receiving said transmitted scan image and displaying said scan image and having an input connected to said display output of said computer means; and an imaging scan display system having an input connected to receive said output position signal from said electromagnetic position indicating means and adapted to display a scan image associated with a three dimensional position of said reference position in said surgical field.

5. A locating device for use with a stereotactic device comprising:

electromagnetic position indicating mean for generating an output position signal identifying the location of a reference position with respect to a surgical field, and wherein said electromagnetic position indicating means further comprises:

electromagnetic transmitter means for transmitting electromagnetic energy;

an electromagnetic receiver means for receiving electromagnetic energy;

magnetic field digitization means having an input connected to said electromagnetic receiver means, a first output connected to said electromagnetic transmitter means, and a second output for outputting a position signal;

computer means for identifying and transmitting a scan image associated with the position of said reference position and having and input connected to said second output of said magnetic field digitization means, a data input, and a display output; and display means for receiving said transmitted scan image and displaying said scan image and having an input connected to said display output of said computer means;

an imaging scan display system having an input connected to receive said output position signal from said electromagnetic position indicating means and adapted to display a scan image associated with a three dimensional position of said reference position in said surgical field; and calibration means for providing a spatial position reference for said electromagnetic receiver means.

* * * * *